United States Patent [19]

Mason et al.

[11] 4,222,936

[45] Sep. 16, 1980

[54] 3-AZABICYCLO(3.1.0)HEXANE-2-CARBONI-TRILE

[75] Inventors: Ronald F. Mason, Westwell nr. Ashford; Barry R. J. Devlin, Sittingbourne, both of England

[73] Assignee: Shell Oil Company, Houston, Tex.

[21] Appl. No.: 26,150

[22] Filed: Apr. 2, 1979

[30] Foreign Application Priority Data

Apr. 20, 1978 [GB] United Kingdom ............... 15677/78

[51] Int. Cl.$^2$ ........................................... C07D 201/52
[52] U.S. Cl. ..................... 260/326.62; 260/326.5 B; 71/95
[58] Field of Search ................................... 260/326.62

[56] References Cited

U.S. PATENT DOCUMENTS 4,047,930   9/1977   Kerr ........................................ 71/76

OTHER PUBLICATIONS

Achini et al., Chemical Abstracts, 87, 84811x (1977), abstract of Ger. Offen. 2,653,251, Jan. 8, 1977.

*Primary Examiner*—Donald G. Daus
*Assistant Examiner*—D. B. Springer

[57] ABSTRACT

Certain 3-azabicyclo(3.1.0)hexane-2-carbonitriles, and a method for their preparation.

1 Claim, No Drawings

3-AZABICYCLO(3.1.0)HEXANE-2-CARBONITRILE

BACKGROUND OF THE INVENTION

3-Azabicyclo(3.1.0)hexane-2-carboxylic acid and certain of its congeners have been found to be plant male gametocides: U.S. Pat. No. 4,047,930 (the compounds are designated therein as 2-carboxy-3,4-methanopyrrolidines).

DESCRIPTION OF THE INVENTION

It has been found that 3-azabicyclo(3.1.0)hexane-2-carboxylic acid can be prepared by:

(1) reducing 3-azabicyclo(3.1.0)hexan-4-one-2-carbonitrile to form 3-azabicyclo(3.1.0)hexane-2-carbonitrile;

(2) converting the 3-azabicyclo(3.1.0)hexane-2-carbonitrile to 3-azabicyclo(3.1.0)hexane-2-carboxylic acid:

(a) by treating the nitrile with barium hydroxide to form the barium salt of the acid, then treating the salt with sulfuric acid;

(b) by treating the nitrile with hydrochloric acid.

This invention is the novel 3-azabicyclo(3.1.0)hexane-2-carbonitrile (2-cyano-3-azabicyclo(3.1.0)hexane) intermediate, and a method for its preparation.

This novel intermediate is described by the formula:

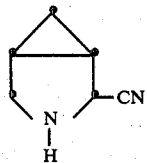

(I)

The compound of Formula I forms acid addition salts with organic and inorganic acids. Salts suitable for the purposes of the invention include salts with mineral acids, for example hydrohalide, especially hydrochloride, salts. Acid addition salts should, of course, be prepared under conditions which do not hydrolyze the 2-cyano group.

The compound of the invention can be prepared by treating a compound of the formula:

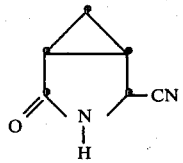

(II)

with a trialkyloxoniumtetrafluoroborate, and treating the resulting product with a suitable reducing agent.

The treatment of the compound of Formula II with a trialkyloxonium tetrafluoroborate produces a fluoroborate complex, which may be isolated, for example by crystallization, or used in situ for the subsequent reduction. Suitably the treatment is carried out at a temperature in the range of from 0° to 30° C., for example at room temperature. The reaction may conveniently be carried out in the presence of a suitable solvent, for example a liquid alkane or halogenated alkane, for example, pentane, hexane, methylene chloride, chloroform or carbon tetrachloride. Mixtures of solvents may be suitable.

The trialkyloxonium tetrafluoroborate may, for example, be trimethyloxonium tetrafluoroborate, triethyloxonium tetrafluoroborate, or a mixed lower alkyl oxonium tetrafluoroborate.

The subsequent reduction step is carried out using a mild reducing agent, for example, a simple or complex alkali metal hydride, such as sodium hydride, lithium hydride, lithium borohydride or, expecially, sodium borohydride. Preferably, the reduction is carried out a room temperature. The reducing agent may be added directly to the reaction mixture obtained in the previous step, or it may be reacted with the tetrafluoroborate complex which has been isolated and dissolved or suspended in a suitable solvent, such as methanol or ethanol. The reaction mixture may be worked up by conventional procedures.

The compound of Formula II is the subject of Ser. No. 14,528. As described therein, it can be prepared by treating a cyclopropyl derivative of the formula

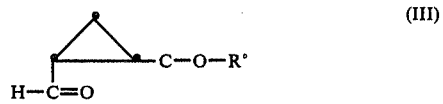

(III)

wherein $R^o$ is an alkali metal, alkaline earth metal, ammonium- or alkyl-substituted ammonium ion, or optionally substituted alkyl, and the formyl group has a cis-relationship with the $COOR^o$ group, with a cyanide in the presence of ammonia.

Suitable cyanides include, for example, hydrogen cyanide, cyanide-containing salts as well as compounds which can generate hydrogen cyanide. Examples of cyanide containing salts are alkali cyanides such as sodium or potassium cyanide as well as ammonium cyanide or alkyl substituted ammonium cyanides such as tri- or tetramethyl ammonium cyanide. Examples of compounds which can generate hydrogen cyanide are aldehyde and ketone cyanohydrins such as acetone cyanohydrin, methyl ethyl ketone cyanohydrin and acetaldehyde cyanohydrin.

Conveniently hydrogen cyanide is added to a cooled solution of the cyclopropyl derivative. When using a cyanide-containing salt, such as sodium or potassium cyanide, the treatment is conveniently carried out in the additional presence of an ammonium halide, such as ammonium chloride or bromide, which will enhance the formation of ammonium cyanide in the reaction mixture. Good results are obtained as a rule when the cyanide is used in a slight molar excess, e.g., 3–10%, in particular 4–7%, based on the cyclopropyl derivative.

The ammonium may be present in the solution containing the cyclopropyl derivative prior to addition of the cyanide, but it can also be added to a mixture already containing a cyanide, which may be in the form of liquid hydrogen cyanide or as a cyanide-containing salt or as a compound which can generate a cyanide. Best results are obtained by saturating a cooled solution of the cyclopropyl derivative and liquid hydrogen cyanide with ammonia. It is advantageous to add ammonia slowly and continuously during the course of the reaction.

The addition of the cyanide and/or the ammonia to the solution of the cyclopropyl derivative is preferably carried out at relatively low temperatures, i.e., at a temperature below 15° C., preferably below 5° C., in order to optimise the uptake of the reactant concerned. When the reactants have been put together an exothermic reaction will normally occur, sometimes after allowing the reaction mixture to reach ambient temperature. The reaction is normally completed by heating the reaction mixture at a temperature up to 80° C., preferably under reflux conditions.

A small amount of a base such as an amine, preferably a tertiary amine having up to 10 carbon atoms, e.g., triethylamine or triethanolamine, or a secondary amine having up to 10 carbon atoms, e.g., piperidine or diethylamine, may also be included in the reaction mixture, as it has a catalytic effect on the reaction. The amount of the base applied generally lies in the range 0.3–10%, preferably 2–6% based on the weight of the cyclopropyl derivative employed.

The process can be carried out conveniently in a solvent. Suitable solvents comprise aliphatic alcohols, such as methanol, ethanol, isopropyl alcohol, 2-chloroethanol and ethylene glycol, ethers such as tetrahydrofuran, or aliphatic nitriles such as acetonitrile. Very good results have been obtained with ethanol as the solvent. Mixtures of two or more solvents and/or of inert diluents can also be used. It is also possible to use an excess of ammonia or hydrogen cyanide as a solvent or co-solvent.

The process is normally carried out at atmospheric pressure. If required, superatmospheric pressures, e.g., up to 10 atmospheres may be employed, however.

The product of the process usually is a mixture of the cis-and trans-isomers, which isomers each consist of the optical isomers. For preparing 3-azabicyclo(3.1.0)hexane-2-carbonitrile, the cis/trans isomer mixtures, or the individual isomers can be used. The individual isomers can be isolated from the appropriate mixtures by fractional crystallization techniques, e.g., by preferential crystallization from ethanol or by fractional chromatographic techniques such as thin layer or column chromatography, using the appropriate carriers and eluent(s).

The cyclopropyl derivatives which are the starting materials can be conveniently prepared by methods known in the art. A suitable method comprises for instance the reaction of an olefinic compound and a sulphur ylid as described in U.S. Pat. No. 3,397,223. Thus, ethyl-2-formylcyclopropanecarboxylate can be prepared by adding acrolein to a solution of ethyl(dimethylsulfuranylidene)acetate in acetone.

The compound of this invention exists in the form of geometric and optical isomers. Thus the -CN group in the 2-position of the molecule may be cis or trans with respect to the three-membered ring, and each of these isomers exists as a pair of optical isomers. The invention includes individual isomers and mixtures thereof.

If a mixture of isomers of the compound of Formula II is used as starting material, the process according to the invention generally leads to a mixture of isomers of the compound of Formula I, which may, if desired, be separated into individual isomers or groups of isomers by conventional methods. For example, cis and trans isomers may be separated by fractional crystallization or layer or column chromatography. However, depending on the isomer desired it may be advantageous to start from a particular isomer of a compound of Formula II. Especially preferred is cis (d,l) 2-cyano-3-azabicyclo(3.1.0)hexane, which may for example be obtained from cis (d,l) 2-cyano-3-azabicyclo(3.1.0)hexan-4-one.

The compound of Formula I is a useful intermediate compound in the preparation of 2-carboxy-3-azabicyclo(3.1.0)hexane and certain of its derivatives. These compounds, for example those described in U.S. Pat. No. 4,047,930, exhibit interesting pollen suppressant and plant growth regulating activity. For example 2-cyano-3-azabicyclo(3.1.0)-hexane can be converted into the corresponding acid by hydrolysis, using for example a mineral acid, or into an ester, by reaction with an alcohol. Particular isomers of 2-carboxy-3-azabicyclo(3.1.0)hexane and its derivatives may be obtained. For example, trans (d,l) 2cyano-3-azabicyclo(3.1.0)hexane can be converted into trans (d,l) 2-carboxy-3-azabicyclo(3.1.0)hexane by acid hydrolysis or into trans (d,l) 2-ethoxycarbonyl-3-azabicyclo(3.1.0)hexane by reaction with ethanol. The compound of the present invention can also be converted into corresponding thioamides by reaction with hydrogen sulphide or a mono- or di-alkyl sulphide in the presence of a tertiary amine.

The compound of Formula I exhibits herbicidal activity. The present invention, therefore, also provides a herbicidal composition comprising a carrier and/or surface active agent, characterized in that it contains as active ingredient the compound of Formula I. The invention also provides a method of controlling undesired plant growth at a locus, characterized in that there is applied to the locus a herbicidally effective amount of the compound of Formula I or a composition according to the invention.

Any of the carrier materials or surface-active agents usually applied in formulating pesticides may be used in the compositions according to the present invention. Examples of such carriers and surface-active agents are given in British Patent Specification No. 1,293,546.

Preparation of 3-azabicyclo(3.1.0)hexane-2-carbonitrile in particular instances, and is conversion to 3-azabicyclo(3.1.0)hexane-2-carboxylic acid, is demonstrated in the following examples.

EXAMPLE 1

A mixture of 21.3 g of cis ethyl 2-formylcyclopropanecarboxylate, 50 ml of absolute ethanol and 4 drops of piperidine was cooled to 0° C. 6 ml (4.2 g) of hydrogen cyanide was added, the mixture was saturated with anhydrous ammonia, and the resulting mixture was allowed to warm to room temperature. After the addition of further ammonia the temperature rose slowly and the mixture was kept at 70°–75° C. for 45 minutes. After removal of the volatile components in a film evaporator under reduced pressure, the remaining mixture was saturated with ethanol under cooling in an ice bath, then filtered and recrystallized from 30 ml ethanol to give a solid, mp 135°–136° C. The product was characterized by elemental analysis, and by proton and $C^{13}$ magnetic resonance spectroscopy as pure cis 3-azabicyclo(3.1.0)hexan-4-one-2-carbonitrile.

A further amount of that compound, as a mixture of cis and trans isomers, was obtained by chromatographing the mother liquor over silica gel, using methylene dichloride as eluent. An analytically pure sample of the trans isomer, mp 89°–90° C., was obtained using liquid-liquid chromatography. The compound was characterized by nuclear magnetic spectroscopy.

Similar results were obtained when the reaction was carried out using 95.85 g of cis ethyl 2-formylcyclopropanecarboxylate as starting material. (66% of cis/-trans product was isolated).

EXAMPLE 2

10 g of cis 3-azabicyclo(3.1.0)hexan-4-one-2-carbonitrile was dissolved in 50 ml of dry methylene chloride, and 19 g of triethyloxonium tetrafluoroborate was added to the stirred solution at 10°-15° C. The resulting mixture was stirred for 18 hours, then the volatile materials were evaporated under reduced pressure. The residue was dissolved in dry ethanol; and the solution was cooled to 5°-10° C. and 4.0 g of sodium borohydride was added in portions thereto over a ten-minute period. The resulting mixture was stirred for 20 hours at room temperature. The volatile materials were evaporated. 150 ml of water was added to the residue and the resulting solution was extracted with ether. The extract was dried (MgSO$_4$) and the solvent was evaporated. The residue, crude 3-azabicyclo(3.1.0)hexane-2-carbonitrile, was dissolved in 80 ml of 6 N hydrochloric acid and the solution was refluxed for four hours. The water was evaporated until the volume of the mixture was 20 ml, when it was poured down a column of Dowex W-X8 and washed free of chloride ions. The product was eluted with 2 N ammonium hydroxide, collecting a total volume of 3 liters. Evaporation of the volatile materials gave a syrup. 100 ml of ethanol was added; the mixture was heated and filtered. Evaporation of the volatile materials gave a pale yellow oil which solidified at 1 Torr. pressure. The NMR and IR spectra of that product were identical to the naturally-occurring cis 3-azabicyclo(3.1.0)hexane-2-carboxylic acid, the cis content of the product being greater than 90%.

In a similar experiment, starting from 4.5 g cis 3-azabicyclo-(3.1.0)hexan-4-one-2-carbonitrile, a semi-solid residue was obtained, to which benzene was added. Evaporation of the benzene left a yellow oil which gave, on distillation, cis 3-azabicyclo(3.1.0)hexane-2-carboxylic acid, as a liquid, bp 80°-86° C. at 1 Torr. pressure.

EXAMPLE 3

18 g of a mixture of 45% cis and 55% trans 3-azabicyclo(3.1.0)hexan-4-one-2-carbonitrile was mixed with 250 ml of dry methylene chloride. The mixture was stirred and 32 g of triethyloxonium tetrafluoroborate was added in portions. Cooling was not required. Upon stirring for 30 minutes, a heavy oil began to separate. The mixture then was stirred for 15 hours at room temperature. The volatile materials were evaporated under reduced pressure. The residue, a yellow oil, was dissolved in 120 ml of dry ethanol. The solution was stirred and cooled to 0° C., and 12.8 g of sodium borohydride was added, in portions. The mixture was stirred overnight, the solvent was evaporated and the residue was treated with 100 ml of water. The resulting mixture was extracted with ether. The ether was evaporated from the extract to leave a viscous yellow oil. The oil was dissolved in benzene, the solution was dried (MgSO$_4$) and the benzene was evaporated. The residue was distilled under reduced pressure to give a product, bp: 56°-60° C., 0.3 Torr, which NMR spectroscopy carried out in hexadeuterobenzene established to contain 91% of the trans isomer and 8% of the cis isomer of 3-azabicyclo(3.1.0)hexane-2-carbonitrile.

EXAMPLE 4

7.0 g of the cis/trans mixture obtained via the procedure described in Example 3 was treated with a cold isopropyl alcohol/petroleum ether mixture from which the trans isomer crystallized in the form of white needles, mp 39°-40° C.

EXAMPLE 5

142 g of a solution of mixed 2-cyano-3-azabicyclo(3.1.0)hexane (cis/trans ratio 45/55) in 140 ml water was cooled to 0° C. and treated with 145 g of ethyl chloroformate over 30 minutes. The temperature was held at 0°-2° C. by isopropanol/dry ice cooling. A solution of 181 g of potassium carbonate in 220 ml water was then added dropwise over 30 minutes with the temperature maintained at 0° to −5° C. Reaction was quite exothermic at this stage. The mixture was warmed to 15° C. over 45 minutes. The layers were separated and the aqueous phase extracted 3 times with diethyl ether. After washing the combined extracts with water to pH 7, the ether was removed on a rotary evaporator to give a crude product.

This material was subjected to vacuum fractionation using a column packed with 15 cm of multi-turn helices. The first fraction obtained was identified using NMR spectroscopy as trans 2-cyano-3-ethoxycarbonyl-3-azabicyclo(3.1.0)hexane. The final fraction obtained was the cis isomer.

EXAMPLE 6

34.6 g of a mixture of the cis and trans isomers of 3-azabicyclo(3.1.0)hexane-2-carbonitrile, 102.8 g of barium hydroxide octahydrate, and 500 ml of water was refluxed for 7 hours. The mixture was cooled, and then was carefully neutralized to pH 6 with 33.2 g of 96% sulfuric acid in 500 ml of water. Celite was added and the mixture was filtered. The solvent was evaporated and the residue was extracted with hot ethanol. The undissolved solid was an approximately 2/1 mixture of trans and cis 3-azabicyclo(3.1.0)hexane-2-carboxylic acid. The solid obtained from evaporation of the solvent from the extract was an approximately 2.2/1 mixture of the cis and trans isomers.

The solid was subjected to chromatography on a cation exchange resin, using 1.5 N hydrochloric acid as eluent, to give the cis isomer as a solid, mp 226°-228° C. (with gas evolution), as the more mobile isomer. The less mobile isomer was the trans isomer, mp 202°-206° C. (with gas evolution).

Demonstration of Herbicidal Activity

To evaluate its herbicidal activity the compound of the invention was tested using as a representative range of plants: maize, *Zea mays* (MZ); barnyard grass, *Echinochloa crusgalli* (BG); oat, *Avena sativa* (O); mustard, *Sinapis alba* (M); sugar beet, *Beta vulgaris* (SB); and soya bean, *Glycine max* (S).

The tests involved were post-emergence tests, involved foliar spray tests in which seedling plants of the above species were sprayed with a liquid formulation containing the compound of the invention.

The soil used in the tests was a steam-sterilized, modified John Innes Compost mixture in which half the peat, by loose bulk, had been replaced by vermiculite.

The formulations used in the tests were prepared by preparing a solution of the compound in acetone containing 0.4% by weight of an alkylphenyl/ethylene oxide condensate available under the trade name TRITON X-155. The acetone solution was diluted with an equal volume of water and the resulting formulation applied at a dosage level corresponding to 5 kilograms of active material per hectare in a volume equivalent to 400 liters per hectare.

The herbicidal effects of the compound was assessed visually seven days after spraying the foliage and eleven days after spraying the soil, and were recorded on a 0–9 scale. A rating 0 indicates no effect on the treated plants, a rating 2 indicates a reduction in growth of the plants of approximately 25%, a rating 5 indicates a reduction of approximately 55%, a rating 9 indicates a reduction of 95%.

The results of the tests are presented in the following Table:

| COMPOUND | PHYTOTOXICITY RATING (0–9 SCALE) | | | | | |
|---|---|---|---|---|---|---|
| | MZ | BG | O | M | SB | S |
| Trans 2-cyano-3-azabicyclo-(3.1.0)hexane | 6 | 5 | 5 | 3 | 3 | 4 |
| 60% cis, 40% trans 2-cyano-3-azabicyclo-(3.1.0)hexane | 2 | 4 | 4 | 2 | 1 | 4 |

We claim:
1. 3-azabicyclo(3.1.0)hexane-2-carbonitrile.

* * * * *